United States Patent
Tachikawa

(10) Patent No.: US 8,049,187 B2
(45) Date of Patent: Nov. 1, 2011

(54) CHARGED PARTICLE BEAM IRRADIATING APPARATUS

(75) Inventor: Toshiki Tachikawa, Niihama (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 412 days.

(21) Appl. No.: 12/411,995

(22) Filed: Mar. 26, 2009

(65) Prior Publication Data

US 2009/0242789 A1    Oct. 1, 2009

(30) Foreign Application Priority Data

Mar. 28, 2008  (JP) ................................ P2008-086554

(51) Int. Cl.
*A61N 5/00*      (2006.01)

(52) U.S. Cl. .......... 250/492.1; 250/396 R; 250/396 ML; 250/492.3; 600/1; 600/2

(58) Field of Classification Search .............. 250/396 R, 250/396 ML, 492.1, 492.3; 600/1, 2
See application file for complete search history.

(56) References Cited

U.S. PATENT DOCUMENTS

2002/0030164 A1*  3/2002  Akiyama et al. ........... 250/492.1
2009/0008575 A1*  1/2009  Okazaki et al. ............ 250/492.1

FOREIGN PATENT DOCUMENTS

| JP | 11-28252 | 2/1999 |
|---|---|---|
| JP | 2006-34701 | 2/2006 |

* cited by examiner

*Primary Examiner* — Michael Maskell

(74) *Attorney, Agent, or Firm* — Squire, Sanders & Dempsey (US) LLP

(57) ABSTRACT

The present invention provides a charged particle beam irradiating apparatus capable of irradiating a charged particle beam using both a wobbler method and a scanning method. A charged particle beam irradiating apparatus includes: scanning electromagnets that scan a charged particle beam; a wobbler irradiation unit that irradiates the charged particle beam using a wobbler method; a scanning irradiation unit that irradiates the charged particle beam using a scanning method; and a control unit that controls the wobbler irradiation unit and the scanning irradiation unit. In the charged particle beam irradiating apparatus, the control unit operates one of the wobbler irradiation unit and the scanning irradiation unit, and controls the other irradiation unit to be in a withdrawn state so as not to hinder the irradiation of the charged particle beam.

6 Claims, 3 Drawing Sheets

CHARGED PARTICLE BEAM IRRADIATING APPARATUS

BACKGROUND OF THE INVENTION

1. Field of the Invention

The present invention relates to a charged particle beam irradiating apparatus that irradiates a charged particle beam to an object.

Priority is claimed on Japanese Patent Application No. 2008-86554, filed Mar. 28, 2008, the content of which is incorporated herein by reference.

2. Description of the Related Art

A charged particle beam irradiating apparatus has been proposed which includes a scanning electromagnet that performs scanning with a charged particle beam and a wobbler irradiation unit that irradiates the charged particle beam using a wobbler method (for example, see JP-A-11-28252). In the charged particle beam irradiating apparatus using the wobbler method, the charged particle beam is circularly irradiated and diffused by the scanning electromagnet. The diffused charged particle beam is shaped according to the shape of an object and then irradiated.

In addition, a charged particle beam irradiating apparatus has been proposed which includes a scanning electromagnet that performs scanning with a charged particle beam and a scanning irradiation unit that irradiates the charged particle beam using a scanning method (for example, see JP-A-2006-34701). In the charged particle beam irradiating apparatus using the scanning method, the charged particle beam is irradiated to an object by the scanning electromagnet to scan the object.

The above-mentioned charged particle beam irradiating apparatuses are independent apparatuses in terms of functions. They can perform either the irradiation operation using the wobbler method or the irradiation operation using the scanning method. Therefore, the charged particle beam irradiating apparatuses have low flexibility in irradiation.

SUMMARY OF THE INVENTION

Therefore, an object of the invention is to provide a charged particle beam irradiating apparatus capable of irradiating a charged particle beam using both a wobbler method and a scanning method.

According to an aspect of the invention, there is provided a charged particle beam irradiating apparatus for irradiating a charged particle beam to an object. The charged particle beam irradiating apparatus includes: a scanning electromagnet that scans the charged particle beam; a wobbler irradiation unit that irradiates the charged particle beam using a wobbler method; a scanning irradiation unit that irradiates the charged particle beam using a scanning method; and a control unit that controls the wobbler irradiation unit and the scanning irradiation unit. The control unit operates one of the wobbler irradiation unit and the scanning irradiation unit, and controls the other irradiation unit to be in a withdrawn state so as not to hinder the irradiation of the charged particle beam.

In the charged particle beam irradiating apparatus, the control unit operates one of the wobbler irradiation unit and the scanning irradiation unit, and controls the other irradiation unit to be in a withdrawn state so as not to hinder the irradiation of the charged particle beam. That is, for example, when the charged particle beam is irradiated by a wobbler method (hereinafter, referred to as 'wobbler irradiation'), the charged particle beam is irradiated so as to draw a circle and diffused by the scanning electromagnet. Then, the control unit operates the wobbler irradiation unit to shape the charged particle beam according to the shape of an object, and the control unit moves the scanning irradiation unit to be in a withdrawn state. On the other hand, when the charged particle beam is irradiated by the scanning method (hereinafter, referred to as 'scanning irradiation'), the charged particle beam is irradiated to an object by the scanning electromagnet. In this case, the control unit operates the scanning irradiation unit to converge the charged particle beam, and the control unit moves the wobbler irradiation unit to be in a withdrawn state. Therefore, according to the above-mentioned aspect of the invention, it is possible to perform irradiation using the wobbler method and irradiation using the scanning method without any adverse effects to either irradiation method. In addition, it is possible to irradiate the charged particle beam using both the wobbler method and the scanning method.

The charged particle beam irradiating apparatus may further include a case to which the wobbler irradiation unit and the scanning irradiation unit are attached. The wobbler irradiation unit may include a charged particle beam shaping unit that shapes the charged particle beam according to the shape of the object. The scanning irradiation unit may include a penetration depth adjusting unit that adjusts the penetration depth of the charged particle beam. The charged particle beam shaping unit and the penetration depth adjusting unit may be interchangeably attached to the case. In this case, when the charged particle beam is irradiated, the charged particle beam shaping unit and the penetration depth adjusting unit can be interchanged to perform both the wobbler irradiation and the scanning irradiation. As such, since the charged particle beam shaping unit and the penetration depth adjusting unit can be interchanged, it is not necessary to attach the units to the charged particle beam irradiating apparatus all the time. Therefore, it is possible to reduce the size of a charged particle beam irradiating apparatus.

The charged particle beam irradiating apparatus may further include at least one of a first switch that is turned on or off when the charged particle beam shaping unit is attached to the case and a second switch that is turned on or off when the penetration depth adjusting unit is attached to the case. The control unit may control the scanning electromagnet on the basis of the states of the first and second switches. In this case, it is possible to identify a unit attached to the case using the first and second switches. Therefore, it is possible to prevent an erroneous operation and a malfunction when the wobbler irradiation and the scanning irradiation are switched with each other (so-called interlock).

The wobbler irradiation unit may include a collimator that has an opening with a variable shape formed therein. The collimator may allow the charged particle beam to pass through the opening to shape the planar shape of the charged particle beam. When operating the scanning irradiation unit, the control unit may move the collimator to an upstream side in an irradiation direction and expand the opening of the collimator. In this way, it is possible to ensure a wide irradiation field during scanning irradiation, and it is possible to appropriately withdraw the collimator.

The wobbler irradiation unit may include a filter that adjusts the dose distribution of the charged particle beam. The filter may include a transmission portion that transmits the charged particle beam without any change. When operating the scanning irradiation unit, the control unit may move the filter such that the charged particle beam passes through the transmission portion. In this case, during scanning irradiation, the filter is moved such that the charged particle beam passes through the transmission portion. In this way, the filter can be in a withdrawn state.

The wobbler irradiation unit may include a scatterer that is provided on a downstream side of the scanning electromagnet and diffuses the charged particle beam. A portion of the passage of the charged particle beam that is disposed on the upstream side of the scatterer may be vacuum sealed. During scanning irradiation, the charged particle beam is converged and irradiated. Therefore, it is preferable to vacuum seal the passage of the charged particle beam. This is because the vacuum passage of the charged particle beam can prevent the diffusion of the charged particle beam. On the other hand, during wobbler irradiation, the charged particle beam is diffused and irradiated. Therefore, as described above, the wobbler irradiation unit may include a scatterer. It is difficult to arrange the scatter in a vaccum chamber in terms of a structural restriction, such as a large size (thickness). Therefore, in general, the scatter is arranged in the air. Therefore, in the above-mentioned aspect of the invention, the scatterer is arranged on the downstream side of the scanning electromagnet, and the passage of the charged particle beam on the upstream side of the scatterer is vacuum sealed. In this way, during wobbler irradiation, the scatterer can diffuse the charged particle beam, and during scanning irradiation, it is possible to prevent the diffusion of the charged particle beam.

According to the above-mentioned aspect of the invention, it is possible to irradiate a charged particle beam using both a wobbler method and a scanning method.

DESCRIPTION OF THE PREFERRED EMBODIMENTS

Figure 1:
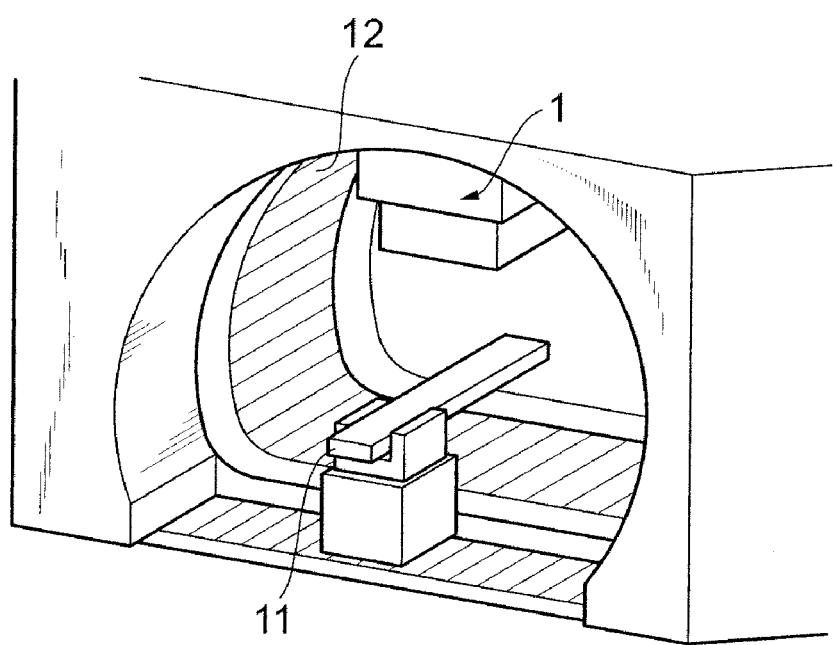
FIG. 1 is a perspective view illustrating a charged particle beam irradiating apparatus according to an embodiment of the invention.

Hereinafter, exemplary embodiments of the invention will be described in detail with reference to the accompanying drawings. In the following description, the same or equivalent components are denoted by the same reference numerals, and a repetitive description thereof will be omitted.

FIG. 1 is a perspective view illustrating a charged particle beam irradiating apparatus according to an embodiment of the invention. As shown in FIG. 1, a charged particle beam irradiating apparatus 1 is provided on a rotating gantry 12 that is provided so as to surround a treatment table 11. The charged particle beam irradiating apparatus 1 can be rotated around the treatment table 11 by the rotating gantry 12.

Figure 2:
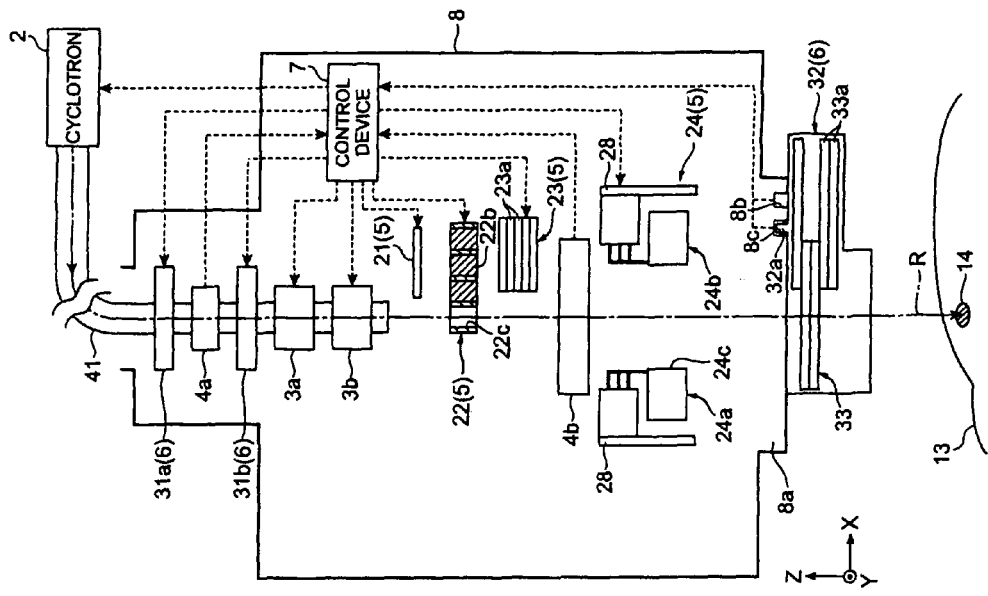
FIG. 2 is a diagram schematically illustrating the charged particle beam irradiating apparatus shown in FIG. 1 during wobbler irradiation.
Figure 3:
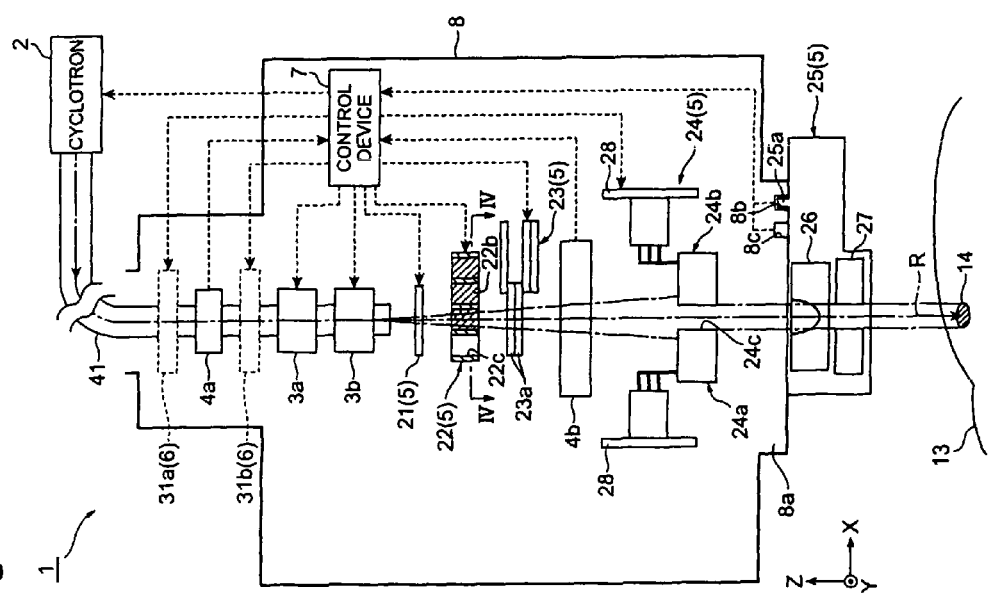
FIG. 3 is a diagram schematically illustrating the charged particle beam irradiating apparatus shown in FIG. 1 during scanning irradiation.

FIG. 2 is a diagram schematically illustrating the structure of the charged particle beam irradiating apparatus shown in FIG. 1 during wobbler irradiation, and FIG. 3 is a diagram schematically illustrating the structure of the charged particle beam irradiating apparatus shown in FIG. 1 during scanning irradiation. As shown in FIGS. 2 and 3, the charged particle beam irradiating apparatus 1 irradiates a charged particle beam R to a tumor (object) 14 in the body of a patient 13 using two irradiation methods, such as a wobbler method and a scanning method. The charged particle beam R is obtained by accelerating charged particles at a high speed. For example, a proton beam or a heavy particle (heavy ion) beam is used as the charged particle beam R. The wobbler method is also called a broad beam method.

As shown in FIGS. 2 and 3, the charged particle beam irradiating apparatus 1 includes a cyclotron 2, scanning electromagnets 3a and 3b, monitors 4a and 4b, a wobbler irradiation unit 5, a scanning irradiation unit 6, and a control device 7.

The cyclotron 2 is a generation source that generates the charged particle beam R. The cyclotron 2 is connected to the control device 7, and the supply of a current to the cyclotron 2 is controlled by the control device. The scanning electromagnets 3a and 3b change a magnetic field corresponding to the current supplied from the control device 7 to scan the charged particle beam R. The scanning electromagnet 3a scans the charged particle beam R in the X direction, and the scanning electromagnet 3b scans the charged particle beam R in the Y direction. The scanning electromagnets 3a and 3b are sequentially arranged on the downstream side of the cyclotron 2 in the direction of the irradiation axis of the charged particle beam R (hereinafter, simply referred to as a 'radiation axis').

The monitor 4a monitors the position of the charged particle beam R, and the monitor 4b monitors the absolute value of the dose of the charged particle beam R and the dose distribution of the charged particle beam R. The monitors 4a and 4b output monitoring information to the control device 7. The monitor 4a is arranged on the upstream side of the scanning electromagnet 3a on the downstream side of the cyclotron 2 in the direction of the irradiation axis. The monitor 4b is arranged on the downstream side of the scanning electromagnet 3b in the direction of the irradiation axis.

The wobbler irradiation unit 5 is for irradiating a charged particle beam using the wobbler method, and is attached and held by a case 8. The wobbler irradiation unit 5 includes a scatterer 21, a ridge filter 22, a fine degrader 23, and a multi-leaf collimator 24.

The scatterer 21 diffuses the traveling charged particle beam into a wide beam that is spread in a direction orthogonal to the irradiation axis. The scatterer 21 has a plate shape with a thickness of, for example, several millimeters and is made of lead. The scatterer 21 is arranged on the upstream side of the monitor 4b on the downstream side of the scanning electromagnet 3b in the direction of the irradiation axis. In addition, the scatterer 21 is moved so as to be away from the irradiation axis during scanning irradiation under the control of the control device 7, such that the charged particle beam R does not pass through the scatterer (see FIG. 3). That is, during scanning irradiation, the scatterer 21 is in a withdrawn state so that it does not hinder the irradiation of the charged particle beam R.

The ridge filter 22 is for adjusting the dose distribution of the charged particle beam R. Specifically, the ridge filter 22 gives a spread-out Bragg peak (SOBP) to the charged particle beam R so as to correspond to the thickness of the tumor 14 in the body of the patient 13 (the length of the tumor in an irradiation direction).

Figure 4:
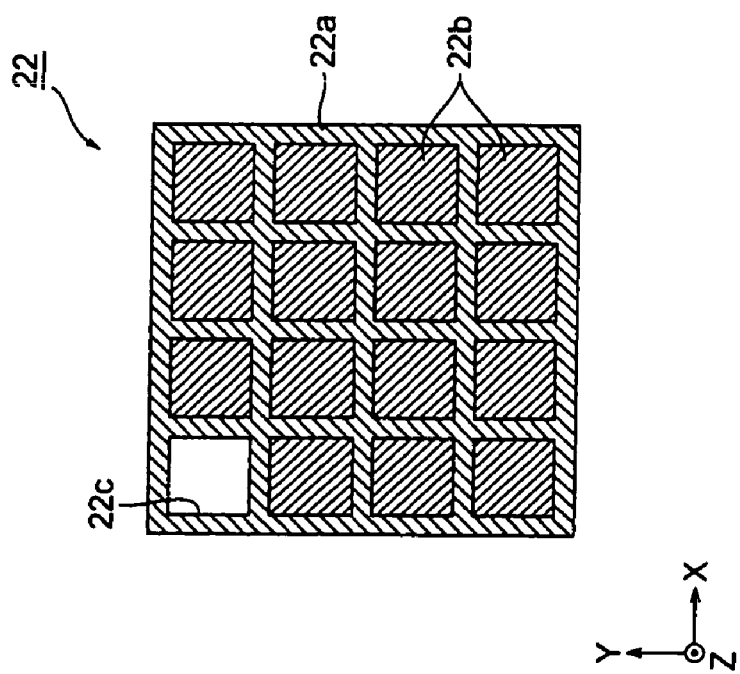
FIG. 4 is a cross-sectional view illustrating a ridge filter taken along the line IV-IV of FIG. 2.

FIG. 4 is a cross-sectional view illustrating the ridge filter taken along the line IV-IV of FIG. 2. As shown in FIG. 4, the ridge filter 22 includes a plurality of filter portions 22b arranged in a matrix on a stage 22a. The filter portion 22b is formed by arranging metal rods having thicknesses that vary stepwise in parallel to each other like a bamboo blind, and different SOBPs are formed by the shapes of the metal rods. A blank portion (transmission portion) 22c, which is an opening that does not give the SOBP to the charged particle beam R but transmits the charged particle beam R without any change, is provided in the stage 22a. The ridge filter 22 is moved by the control device 7 such that the filter portion 22b transmitting the charged particle beam R is selectively changed. In this way, it is possible to adjust the width and the position of the SOBP of the charged particle beam R.

Returning to FIGS. 2 and 3, the ridge filter 22 is arranged on the upstream side of the monitor 4b on the downstream side of the scatterer 21 in the direction of the irradiation axis. In addition, during scanning irradiation, the ridge filter 22 is moved by the control device 7 such that the charged particle beam R passes through the blank portion (transmission portion) 22c (see FIG. 3). That is, the ridge filter 22 is in a withdrawn state during scanning irradiation.

The fine degrader 23 changes the energy loss of the traveling charged particle beam R to adjust the penetration depth of the charged particle beam R in the body of the patient 13. Specifically, the fine degrader 23 includes a plurality of blocks 23a laminated to each other, and adjusts a direction in which the blocks overlap each other to change the thickness of the blocks transmitting the charged particle beam R. In this way, the energy loss of the charged particle beam R varies depending on the thickness of the blocks 23a transmitting the charged particle beam. As a result, the penetration depth is changed.

The fine degrader 23 is arranged between the ridge filter 22 and the monitor 4b in the direction of the irradiation axis. In addition, during scanning irradiation, the fine degrader 23 is moved by the control device 7 such that the blocks 23a are away from the irradiation axis. As a result, the charged particle beam R does not pass through the blocks 23a (see FIG. 3). That is, the fine degrader 23 is in a withdrawn state during scanning irradiation.

The multi-leaf collimator (hereinafter, referred to as an 'MLC') 24 is for shaping the charged particle beam R (planar shape) in a plane direction that is vertical to the irradiation direction, and includes beam shielding portions 24a and 24b each having a plurality of comb teeth. The beam shielding portions 24a and 24b are arranged so as to be engaged with each other, and an opening 24c is formed between the beam shielding portions 24a and 24b. The MLC 24 allows the charged particle beam R to pass through the opening 24c to shape the charged particle beam R into an outline corresponding to the shape of the opening 24c.

The MLC 24 can move the beam shielding portions 24a and 24b in a direction that is orthogonal to the irradiation axis to change the position and the shape of the opening 24c. In addition, the MLC 24 is guided in the irradiation direction by a linear guide 28 such that it can be moved in the irradiation direction.

The MLC 24 is arranged on the downstream side of the monitor 4b in the direction of the irradiation axis. In addition, during scanning irradiation, the MLC 24 is controlled by the control device 7 such that the opening 24c extends and the MLC is moved to the upstream side in the direction of the irradiation direction (see FIG. 3). In this case, during scanning irradiation, the opening 24c extends so as to have a maximum opening area and the MLC 24 is moved to the upper limit. That is, the MLC 24 is in the withdrawn state during scanning irradiation.

The wobbler irradiation unit 5 further includes a snort holder (charged particle beam shaping unit) 25. The snort holder 25 is prepared for each patient 13 in advance during wobbler irradiation. The snort holder 25 is detachable from the leading end 8a of the case 8 in the irradiation direction, and can be replaced with a fine degrader holder 32, which will be described below. The snort holder 25 includes a bolus 26 and a patient collimator 27.

The bolus 26 forms the three-dimensional shape of the deepest portion which the charged particle beam R reaches according to the shape of the deepest portion of the tumor 14. The shape of the bolus 26 is calculated on the basis of, for example, the outline of the tumor 14 and the electron density of a peripheral tissue obtained from X-ray CT data. The bolus 26 is arranged on the downstream side of the MLC 24 in the direction of the irradiation axis. The patient collimator 27 finally forms the shape of the charged particle beam R in a plan view according to the shape of the tumor 14 in a plan view. The patient collimator 27 is arranged on the downstream side of the bolus 26 in the direction of the irradiation axis, and is used instead of the MLC 24.

The snort holder 25 is provided with a limit switch 25a. When the snort holder 25 is attached to the case 8, the limit switch 25a is inserted into a mounting hole 8b of the case 8 and then turned on. In addition, the limit switch 25a is connected to the control device 7, and outputs switch information to the control device 7.

The scanning irradiation unit 6 is for irradiating a charged particle beam using a scanning method, and is attached or held by the case 8, similar to the wobbler irradiation unit 5. The scanning irradiation unit 6 includes converging members 31a and 31b and a fine degrader holder (penetration depth adjusting unit) 32.

The converging members 31a and 31b converge, for example, the charged particle beam R. In this embodiment, electromagnets are used as the converging members. The converging member 31a is arranged between the cyclotron 2 and the monitor 4a in the direction of the irradiation axis, and the converging member 31b is arranged between the monitor 4a and the scanning electromagnet 3a in the direction of the irradiation axis. In addition, during the wobbler irradiation, the control device 7 stops the supply of a current to the converging members 31a and 31b, and the converging members 31a and 31b are not operated. As a result, the charged particle beam R passes through the converging members 31a and 31b without convergence. That is, the converging members 31a and 31b are in an off state during wobbler irradiation.

The fine degrader holder 32 is detachable from the leading end 8a of the case 8 in the irradiation direction, and can be replaced with the snort holder 25. The fine degrader holder 32 includes a fine degrader 33 therein.

The fine degrader 33 changes the energy loss of the traveling charged particle beam R to finally adjust the maximum penetration depth of the charged particle beam R in the body of the patient 13. Specifically, the fine degrader 33 includes a plurality of blocks 33a laminated to each other in a predetermined direction, and the energy loss of the charged particle beam R varies depending on the thickness of the blocks 33a transmitting the charged particle beam. In this way, the shape of the deepest portion which the charged particle beam R reaches is formed to correspond to the shape of the deepest portion of the tumor 14. In addition, there is a method of changing the energy loss between the cyclotron 2 and the converging member 31a. In this case, the fine degrader 33 is not needed.

The fine degrader holder 32 is provided with a limit switch 32a. When the fine degrader holder 32 is attached to the case 8, the limit switch 32a is inserted into a mounting hole 8c of the case 8 and then turned on. In addition, the limit switch 32a is connected to the control device 7, and outputs switch information to the control device 7.

The control device 7 includes, for example, a CPU, a ROM, and a RAM. The control device 7 controls the cyclotron 2, the scanning electromagnets 3a and 3b, the wobbler irradiation unit 5, and the scanning irradiation unit 6 on the basis of the monitoring information output from the monitors 4a and 4b and the switch information output from the limit switches 25a and 32a (which will be described in detail below).

In addition, in the charged particle beam irradiating apparatus 1, a portion of the passage of the charged particle beam R that is disposed on the upstream side of the scatterer 21 is covered and sealed by a pipe 41, and the pipe 41 is evacuated. For example, the pipe 41 is evacuated by a vacuum pump (not shown) until an internal pressure of $10^{-3}$ [Pa] is obtained.

Next, an operation of irradiating the charged particle beam R to the tumor 14 in the patient 13 using the charged particle beam irradiating apparatus 1 will be described.

In the charged particle beam irradiating apparatus 1, in the case of wobbler irradiation, as shown in FIG. 2, first, the snort holder 25 is attached to the leading end 8a of the case 8. Then, the control device 7 operates the wobbler irradiation unit 5. Specifically, the scatterer 21 is moved such that the charged particle beam R is transmitted, and the ridge filter 22 is moved such that the charged particle beam R passes through the filter portion 22b. In addition, the blocks 23a of the fine degrader 23 are adjusted such that the thickness thereof has a predetermined value, and the beam shielding portions 24a and 24b of the MLC 24 are moved such that the opening 24c has a predetermined shape. The control device 7 controls the converging members 31a and 31b to be turned off.

Then, the cyclotron 2 generates the charged particle beam R. The generated charged particle beam R is circularly irradiated and diffused by the scanning electromagnets 3a and 3b. Then, the charged particle beam R is shaped and adjusted by the ridge filter 22, the fine degrader 23, the MLC 24, the bolus 26, and the patient collimator 27. In this way, the charged particle beam R is irradiated to the tumor 14 in a uniform irradiation field corresponding to the shape of the tumor 14.

When the snort holder 25 is attached to the case 8, the limit switch 25a is turned on, and the control device 7 determines whether the scanning irradiation unit 6 is in a withdrawn state. When it is determined that the scanning irradiation unit 6 is in the withdrawn state, for example, a current having a sine waveform is supplied to the scanning electromagnets 3a and 3b, and the cyclotron 2 generates the charged particle beam R, as described above. On the other hand, when it is determined that the scanning irradiation unit 6 is not in the withdrawn state, no current is supplied to the scanning electromagnets 3a and 3b.

When the limit switch 25a is turned on, the control device 7 controls the scanning electromagnets 3a and 3b. Specifically, a current is supplied to the scanning electromagnets 3a and 3b in a wobbler irradiation mode, and the charged particle beam R is circularly irradiated, as described above.

Furthermore, in the charged particle beam irradiating apparatus 1, in the case of scanning irradiation, as shown in FIG. 3, first, the fine degrader holder 32 is attached to the leading end 8a of the case 8. Then, the control device 7 operates the wobbler irradiation unit 5. Specifically, the converging members 31a and 31b are turned on to converge the traveling charged particle beam R. In addition, the control device 7 withdraws the wobbler irradiation unit 5. As described above, in the method of changing the energy loss between the cyclotron 2 and the converging member 31a, it is not necessary to attach the fine degrader holder 32.

Then, the cyclotron 2 generates the charged particle beam R. The generated charged particle beam R is irradiated to the tumor 14 by the scanning electromagnets 3a and 3b, and passes through the blank portion 22c of the ridge filter 22. Then, the maximum penetration depth of the charged particle beam R is adjusted by the fine degrader 33. In this way, the charged particle beam R is irradiated to the tumor 14 to scan the tumor 14.

When the fine degrader holder 32 is attached to the case 8, the limit switch 32a is turned on, and the control device 7 determines whether the wobbler irradiation unit 5 is in a withdrawn state. When it is determined that the wobbler irradiation unit is in the withdrawn state, for example, a current having a square waveform or a chopping waveform is supplied to the scanning electromagnets 3a and 3b. Then, as described above, the cyclotron 2 generates the charged particle beam R. On the other hand, when it is determined that the wobbler irradiation unit is not in the withdrawn state, no current is supplied to the scanning electromagnets 3a and 3b.

When the limit switch 32a is turned on, the control device 7 controls the scanning electromagnets 3a and 3b. Specifically, a current is supplied to the scanning electromagnets 3a and 3b in the scanning irradiation mode, and the charged particle beam R is irradiated to the tumor 14, as described above.

In the charged particle beam irradiating apparatus 1 according to this embodiment, when the charged particle beam R is irradiated, one of the wobbler irradiation unit 5 and the scanning irradiation unit 6 is operated, and the other unit is withdrawn so as not to hinder the irradiation of the charged particle beam R. Therefore, according to the charged particle beam irradiating apparatus 1, it is possible to perform wobbler irradiation and scanning irradiation without any adverse effects to either irradiation method. In addition, it is possible to irradiate the charged particle beam R using both the wobbler method and the scanning method. As a result, it is possible to improve flexibility in the irradiation of the charged particle beam irradiating apparatus 1. In addition, the scanning electromagnets 3a and 3b can be used in both the wobbler irradiation and the scanning irradiation. Therefore, it is possible to appropriately perform the wobbler irradiation and the scanning irradiation.

As described above, in the charged particle beam irradiating apparatus 1, the snort holder 25 and the fine degrader holder 32 can be interchangeably attached to the case 8. Therefore, when the charged particle beam R is irradiated, the snort holder 25 and the fine degrader holder 32 can be interchanged to perform both the wobbler irradiation and the scanning irradiation. As such, since the snort holder 25 and the fine degrader holder 32 can be interchanged, it is not necessary to attach the holders to the charged particle beam irradiating apparatus 1 all the time. Therefore, it is possible to reduce the size of the charged particle beam irradiating apparatus 1.

Further, in the charged particle beam irradiating apparatus 1, as described above, the snort holder 25 is provided with the limit switch 25a, and the fine degrader holder 32 is provided with the limit switch 32a. The control device 7 controls the scanning electromagnets 3a and 3b on the basis of the switch information of the limit switches 25a and 32a. In addition, the control device 7 determines whether the wobbler irradiation unit 5 or the scanning irradiation unit 6 is in a withdrawn state on the basis of the switch information. In this way, it is possible to identify one of the holders 25 and 32 attached to the case 8, and it is possible to prevent an erroneous operation or a malfunction when wobbler irradiation and scanning irradiation are switched (so-called interlock). As a result, it is possible to prevent the charged particle beam R from being irradiated by an unintended irradiation method, and thus improve the stability of the charged particle beam irradiating apparatus 1.

As described above, during scanning irradiation, the opening 24c of the MLC 24 extends, and the MLC 24 is moved to the upstream side in the irradiation direction. As such, the MLC 24 in a withdrawn state makes it possible to ensure a wide irradiation field during scanning irradiation.

As described above, the blank portion 22c that transmits the charged particle beam R without any change is formed in the ridge filter 22. Therefore, during scanning irradiation, the control device 7 controls the ridge filter 22 to be moved such that the charged particle beam R passes through the blank portion 22c. In this way, it is possible to appropriately withdraw the ridge filter 22.

However, during scanning irradiation, the charged particle beam R is converged and irradiated. Therefore, it is preferable to vacuum seal the passage of the charged particle beam R. This is because the vacuum passage of the charged particle beam R can prevent the diffusion of the charged particle beam R. On the other hand, during wobbler irradiation, the charged particle beam R is diffused and irradiated. Therefore, the wobbler irradiation unit 5 includes the scatterer 21. The scatterer 21 has a volume in the thickness direction thereof, and it is difficult to arrange the scatter in a vacuum chamber in terms of a structural restriction, such as a large size. Therefore, in general, the scatter is arranged in the air. Therefore, in the charged particle beam irradiating apparatus 1, as described above, the scatterer 21 is arranged on the downstream side of the scanning electromagnets 3a and 3b, and a portion of the passage of the charged particle beam R on the upstream side of the scatterer 21 is vacuum sealed. In this way, during wobbler irradiation, the scatterer 21 can diffuse the charged particle beam R, and during scanning irradiation, it is possible to prevent the diffusion of the charged particle beam R. As a result, during scanning irradiation, the scanning electromagnets 3a and 3b can scan the undiffused charged particle beam R, and it is possible to accurately perform scanning irradiation.

As the scanning method of the charged particle beam irradiating apparatus 1, for example, any of the following scanning methods may be used: a spot scanning method of irradiating the charged particle beam R such that an irradiation area has a spot shape; a raster scanning method of continuously irradiating the charged particle beam R in a zigzag to perform scanning; and a line scanning method of continuously irradiating the charged particle beam R in parallel to perform scanning. When the cyclotron 2 is used as in this embodiment, the charged particle beam R is continuously generated. Therefore, it is preferable to use the raster scanning method or the line scanning method as the scanning method. When a synchrotron is used, the charged particle beam R is generated discontinuously (in a pulse manner). Therefore, it is preferable to use the spot scanning method as the scanning method.

Although the exemplary embodiment of the invention has been described above, the invention is not limited to the embodiment. For example, in the above-described embodiment, the holders 25 are 32 are provided with the limit switches 25a and 32a, respectively, but only one of the limit switches 25a and 32a may be provided. In addition, the limit switches 25a and 32a are turned on when the holders 25 and 32 are attached to the case 8. However, the limit switches 25a and 32a may be turned off when the holders 25 and 32 are attached to the case 8.

Furthermore, in the above-described embodiment, the blank portion 22c is formed as a transmission portion in the ridge filter 22. For example, a filter may be used as the transmission portion as long as it can substantially transmit the charged particle beam R without any change.

What is claimed is:

1. A charged particle beam irradiating apparatus for irradiating a charged particle beam to an object, comprising:
    a scanning electromagnet that scans the charged particle beam;
    a wobbler irradiation unit that irradiates the charged particle beam using a wobbler method;
    a scanning irradiation unit that irradiates the charged particle beam using a scanning method; and
    a control unit that controls the wobbler irradiation unit and the scanning irradiation unit,
    wherein the control unit operates one of the wobbler irradiation unit and the scanning irradiation unit, and controls the other irradiation unit to be in a withdrawn state so as not to hinder the irradiation of the charged particle beam.

2. The charged particle beam irradiating apparatus according to claim 1, further comprising:
    a case to which the wobbler irradiation unit and the scanning irradiation unit are attached,
    wherein the wobbler irradiation unit includes a charged particle beam shaping unit that shapes the charged particle beam according to the shape of the object,
    the scanning irradiation unit includes a penetration depth adjusting unit that adjusts the penetration depth of the charged particle beam, and
    the charged particle beam shaping unit and the penetration depth adjusting unit are interchangeably attached to the case.

3. The charged particle beam irradiating apparatus according to claim 2, further comprising:
    at least one of a first switch that is turned on or off when the charged particle beam shaping unit is attached to the case and a second switch that is turned on or off when the penetration depth adjusting unit is attached to the case,
    wherein the control unit controls the scanning electromagnet on the basis of the states of the first and second switches.

4. The charged particle beam irradiating apparatus according to claim 1,
    wherein the wobbler irradiation unit includes a collimator that has an opening with a variable shape formed therein,
    the collimator allows the charged particle beam to pass through the opening to shape the planar shape of the charged particle beam, and
    when operating the scanning irradiation unit, the control unit moves the collimator to an upstream side in an irradiation direction and expands the opening of the collimator.

5. The charged particle beam irradiating apparatus according to claim 1,
    wherein the wobbler irradiation unit includes a filter that adjusts the dose distribution of the charged particle beam,
    the filter includes a transmission portion that transmits the charged particle beam without any change, and
    when operating the scanning irradiation unit, the control unit moves the filter such that the charged particle beam passes through the transmission portion.

6. The charged particle beam irradiating apparatus according to claim 1,
    wherein the wobbler irradiation unit includes a scatterer that is provided on a downstream side of the scanning electromagnet and diffuses the charged particle beam, and
    a portion of the passage of the charged particle beam that is disposed on the upstream side of the scatterer is vacuum sealed.

* * * * *